(12) United States Patent
Huh

(10) Patent No.: US 7,409,723 B2
(45) Date of Patent: Aug. 12, 2008

(54) MULTIFUNCTIONAL PROTECTION RACK FOR SAFETY HELMET

(75) Inventor: Moon Young Huh, Seoul (KR)

(73) Assignee: Otos Tech Co., Ltd., Seoul (KR)

( * ) Notice: Subject to any disclaimer, the term of this patent is extended or adjusted under 35 U.S.C. 154(b) by 641 days.

(21) Appl. No.: 11/054,230

(22) Filed: Feb. 9, 2005

(65) Prior Publication Data

US 2006/0080761 A1    Apr. 20, 2006

(30) Foreign Application Priority Data

Oct. 20, 2004    (KR) .................... 10-2004-0083963

(51) Int. Cl.
*A61F 9/06*    (2006.01)
(52) U.S. Cl. .......................................................... 2/8.2
(58) Field of Classification Search ...................... 2/8.2, 2/2.6, 6.7, 424, 410, 422
See application file for complete search history.

(56) References Cited

U.S. PATENT DOCUMENTS

| | | | | |
|---|---|---|---|---|
| 1,916,678 | A * | 7/1933 | Malcom | 2/8.2 |
| 2,016,775 | A * | 10/1935 | Gingg | 2/8.2 |
| 2,153,714 | A * | 4/1939 | Fleming et al. | 2/8.2 |
| 2,418,334 | A * | 4/1947 | Coccellato | 2/8.2 |
| 3,517,393 | A | 6/1970 | Beauchef | |
| 5,230,101 | A * | 7/1993 | Hedges et al. | 2/424 |
| 5,657,106 | A | 8/1997 | Herald et al. | |
| D393,933 | S | 4/1998 | Huh | |
| 5,771,499 | A | 6/1998 | Monaco et al. | |
| 6,038,707 | A | 3/2000 | Ryden et al. | |
| 6,138,285 | A | 10/2000 | Robrahn et al. | |
| D446,887 | S | 8/2001 | Young | |
| 6,282,726 | B1 * | 9/2001 | Noyerie et al. | 2/424 |

(Continued)

FOREIGN PATENT DOCUMENTS

KR    94-12068    6/1994

(Continued)

OTHER PUBLICATIONS

U.S. Appl. No. 10/062,510, filed Feb. 2, 2002, Huh.

*Primary Examiner*—Danny Worrell
(74) *Attorney, Agent, or Firm*—W. Norman Roth

(57) ABSTRACT

A multifunctional protection rack for a safety helmet having interchangeability, which is connected to the safety helmet to install a welding mask for performing a welding operation, a shade for preventing a direct ray of light from passing therethrough, or a protective shield for preventing foreign substances from being introduced thereinto. The multifunctional protection rack includes a support frame bent into front and rear frames and side support frames, and made of an elastic member formed along the outer surface of a visor of the safety helmet so that the width of the support frame can be adjusted; a first connecting support member, one side of which is connected to the outer surface of the support frame by a rotational angle adjusting portion for adjusting a rotational angle of a protective equipment attached to the protection rack, and the other portion of which is connected to the outer of the support frame by an interval adjusting portion for adjusting an interval between the protective equipment and the face of a worker wearing the safety helmet; and a second connecting support member additionally installed between the support frame and the protective equipment, thereby being installed on the safety helmet such that the protection rack can be opened and closed.

9 Claims, 6 Drawing Sheets

U.S. PATENT DOCUMENTS

| | | |
|---|---|---|
| 6,450,639 B1 | 9/2002 | Abraham |
| D478,111 S | 8/2003 | Huh |
| D481,832 S | 11/2003 | Huh |
| D482,502 S | 11/2003 | Huh |
| D482,503 S | 11/2003 | Huh |

FOREIGN PATENT DOCUMENTS

| | | |
|---|---|---|
| KR | 20320527 | 7/2003 |

* cited by examiner

MULTIFUNCTIONAL PROTECTION RACK FOR SAFETY HELMET

BACKGROUND OF THE INVENTION

1. Field of the Invention

The present invention relates to a multifunctional protection rack for a safety helmet, and more particularly to a multifunctional protection rack for a safety helmet having interchangeability, which is connected to the safety helmet to install a welding mask for performing a welding operation, a light shade for preventing a direct ray of light from passing therethrough, or a protective shield for preventing foreign substances from being introduced thereinto.

2. Description of the Related Art

Workers have increased understanding of safety according to industrial development, and thus protective equipments have been developed now.

Korean Utility Model Laid-open Publication No. 94-12068 discloses a conventional welding mask, which is easily attached to and detached from a safety helmet. The welding mask comprises a transparent window formed through a face portion. A head portion is opened from the upper part of the face portion, and a longitudinal slide hole is formed through the upper part of a side portion so that upper and lower pincers elastically moved by a pincer spring are inserted into a shaft rod through pieces and connected thereto using a butterfly nut. Here, the welding mask has an elastic lock piece and a fixed lock piece installed thereon so that an elastic spring and teeth are engaged with the outer portions of the pieces, thereby being easily installed on the safety helmet.

The above-described welding mask is installed on a visor of the safety helmet, thereby being easily detached from the safety helmet even when a worker changes his/her position.

Further, since the welding mask is opened and closed using the visor of the safety helmet as an axis, weight is concentrated on the front part of the welding mask, thereby damaging the worker's neck.

Korean Utility Model Registration No. 0320527, filed by the present applicant, discloses a sun cap for a safety helmet, which is integrally connected to the safety helmet. The sun cap shades a direct ray of light and prevents foreign substances from being introduced into eyes of a worker by vertical operation of a light shade. The sun cap comprises a band having an elastic coil spring so that the width of a fixing frame surrounding the outer surface of the safety helmet can be adjusted, the light shade connected to the outer part of the band by a fixing member and vertically opened and closed, and the fixing member for integrally connecting the light shade and the band.

The above sun cap is installed on the safety helmet to prevent the direct ray of light and the foreign substances from being introduced into eyes of the worker, and the light shade having a light weight is vertically opened and closed. However, the sun cap has several problems, as follows.

First, the sun cap requires a distance adjusting device for satisfying working conditions of a worker in consideration of a welding position, visibility, and a working posture of the worker.

Second, the sun cap requires a high adhesiveness, which does not change the position of the welding mask at any posture of the worker, and more particularly firmly attaches the heavy sun cap to the safety helmet without separation.

Third, the sun cap requires an ergonomic design, such that the sun cap covers the maximum area of a face of the worker and has a large rotational radius by locating a central shaft of rotation at the rear part of the sun cap so that the center of gravity of the sun cap is the same as the center of gravity of the safety helmet, thereby not damaging the worker's neck.

SUMMARY OF THE INVENTION

Therefore, the present invention has been made in view of the above problems, and it is an object of the present invention to provide a multifunctional protection rack for a safety helmet, which conveniently installs a protective equipment, including a welding mask, on the safety helmet.

It is a further object of the present invention to provide a multifunctional protection rack for a safety helmet, which adjusts a distance with a face of a worker so as to satisfy working conditions of the worker in consideration of a welding position of a welding mask and visibility and a working posture of the worker.

It is another object of the present invention to provide a multifunctional protection rack for a safety helmet, which is detachably attached to any kind of safety helmet and has a high adhesiveness to the safety helmet so that a worker can safely work.

It is yet another object of the present invention to provide a multifunctional protection rack for a safety helmet having an ergonomic structure, which covers the maximum area of a face of a worker and locates a central shaft of rotation at the rear part thereof to have a large rotating radius so that the center of gravity of the protection rack is the same as the center of gravity of the safety helmet, thereby not damaging the worker's neck.

In accordance with the present invention, the above and other objects can be accomplished by the provision of a multifunctional protection rack for a safety helmet comprising: a support frame bent into front and rear frames and side support frames, and made of an elastic member formed along the outer surface of a visor of the safety helmet so that the width of the support frame can be adjusted; a first connecting support member, one portion of which is connected to the outer surface of the support frame by a rotational angle adjusting portion for adjusting a rotational angle of a protective equipment attached to the protection rack, and the other portion of which is connected to the outer of the support frame by an interval adjusting portion for adjusting an interval between the protective equipment and the face of a worker wearing the safety helmet; and a second connecting support member additionally installed between the support frame and the protective equipment, wherein the multifunctional protection rack is installed on the safety helmet such that the protection rack can be opened and closed.

Preferably, the other portion of the first connecting support member may be integrally bent outwardly from the one portion of the first connecting support member.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, preferred embodiments of the present invention will be described in detail with reference to the annexed drawings.

Figure 1:
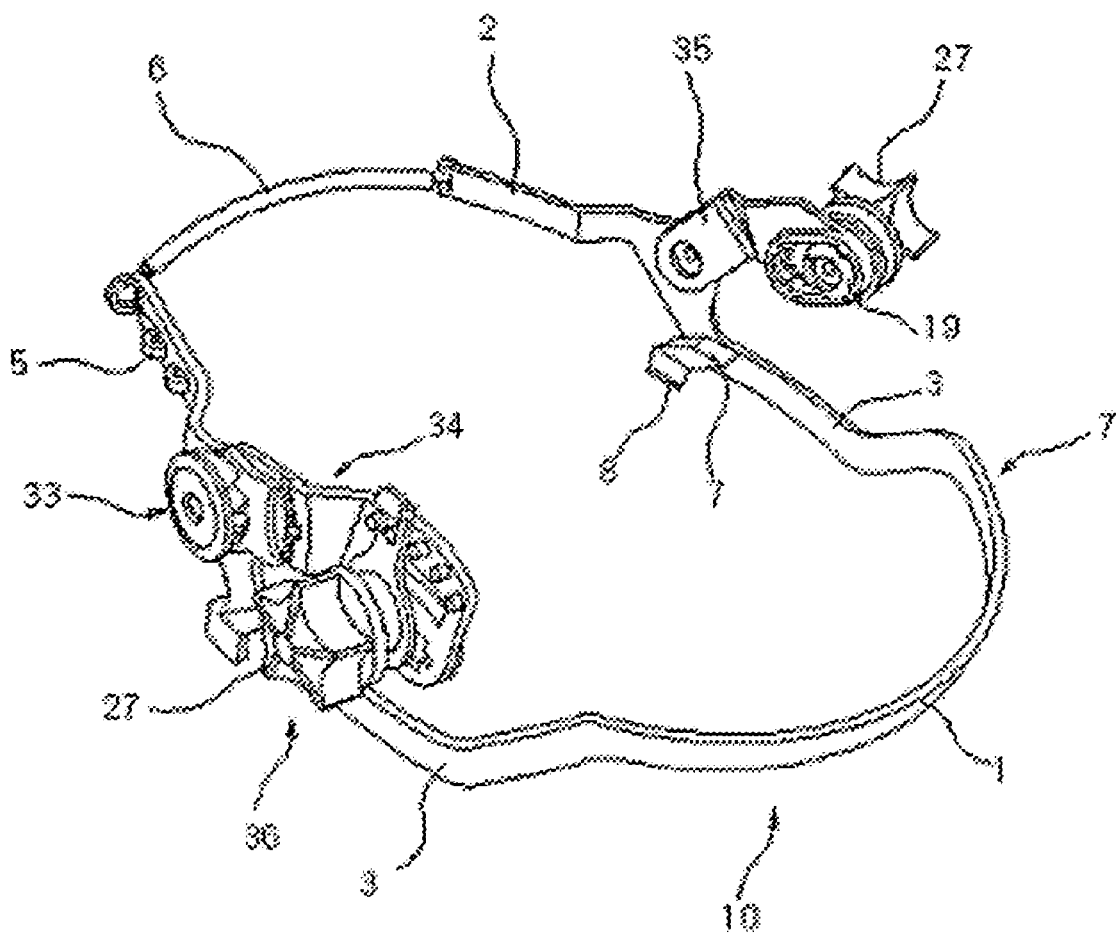
FIG. 1 is a perspective view of a multifunctional protection rack for a safety helmet of the present invention.
Figure 2:
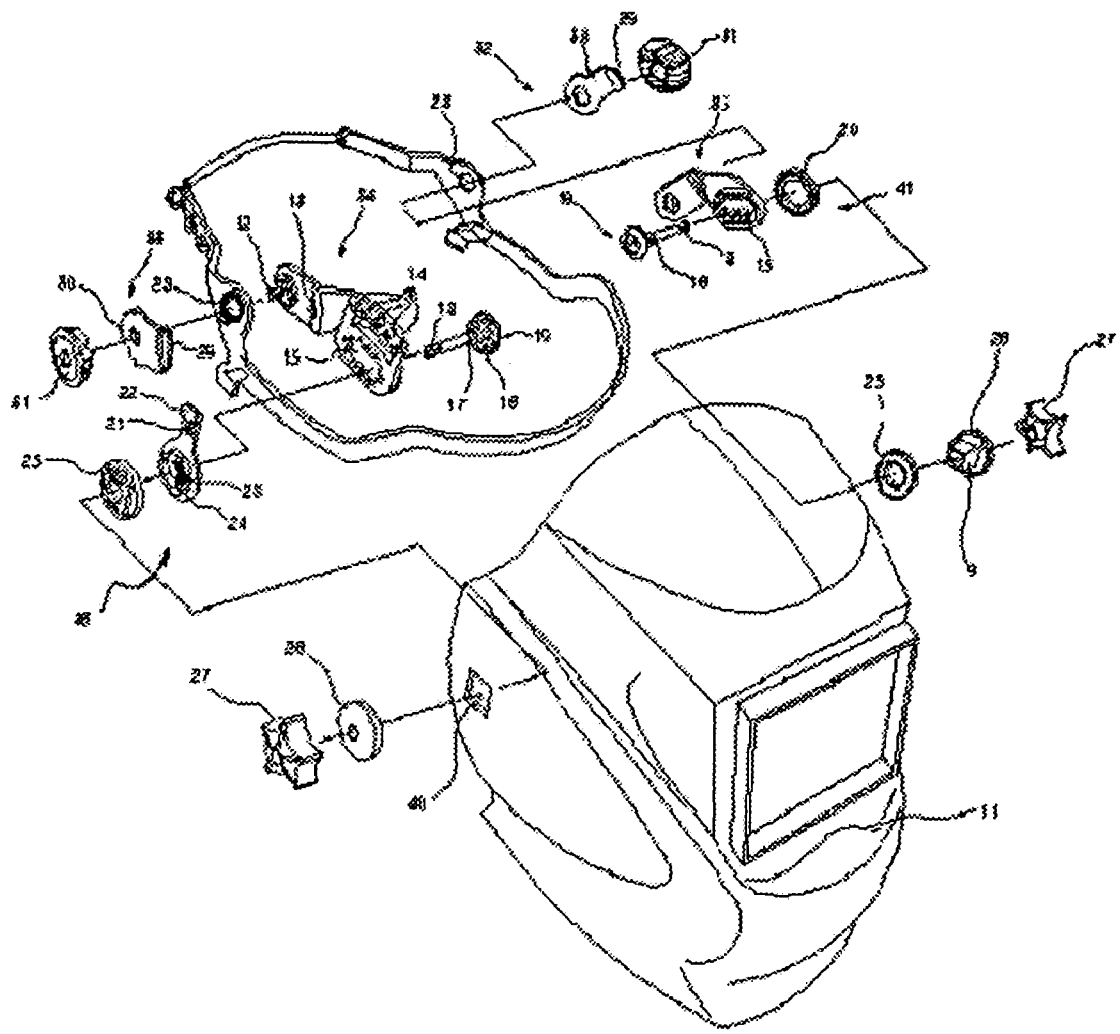
FIG. 2 is an exploded perspective view illustrating connection between a welding mask and the multifunctional protection rack in accordance with a preferred embodiment of the present invention.
Figure 3:
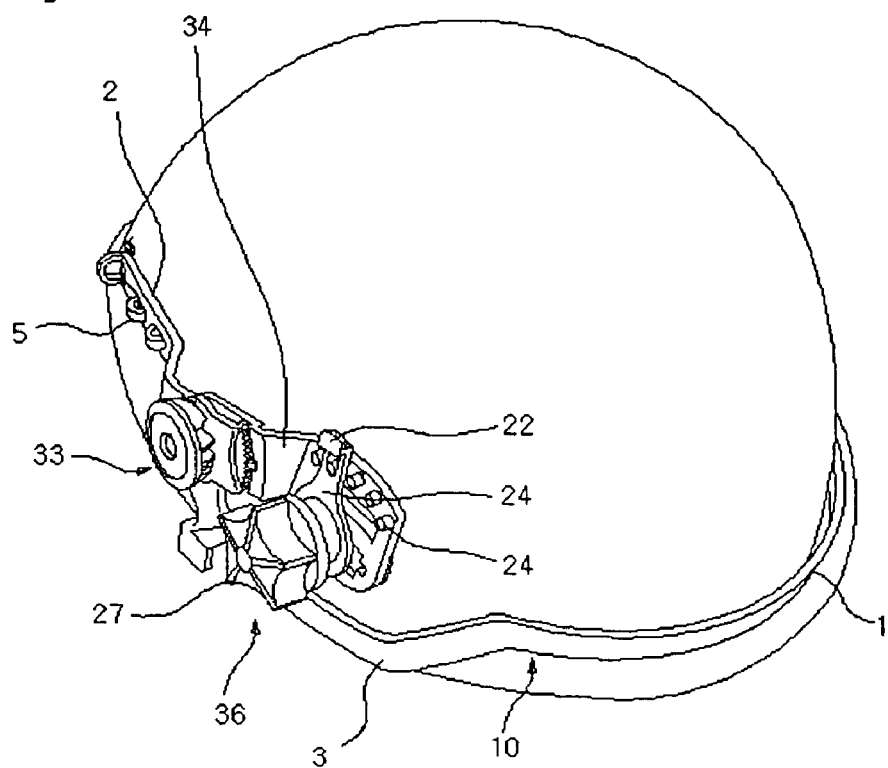
FIG. 3 is a perspective view of the multifunctional protection rack of the present invention, which is installed on a safety helmet.
Figure 4:
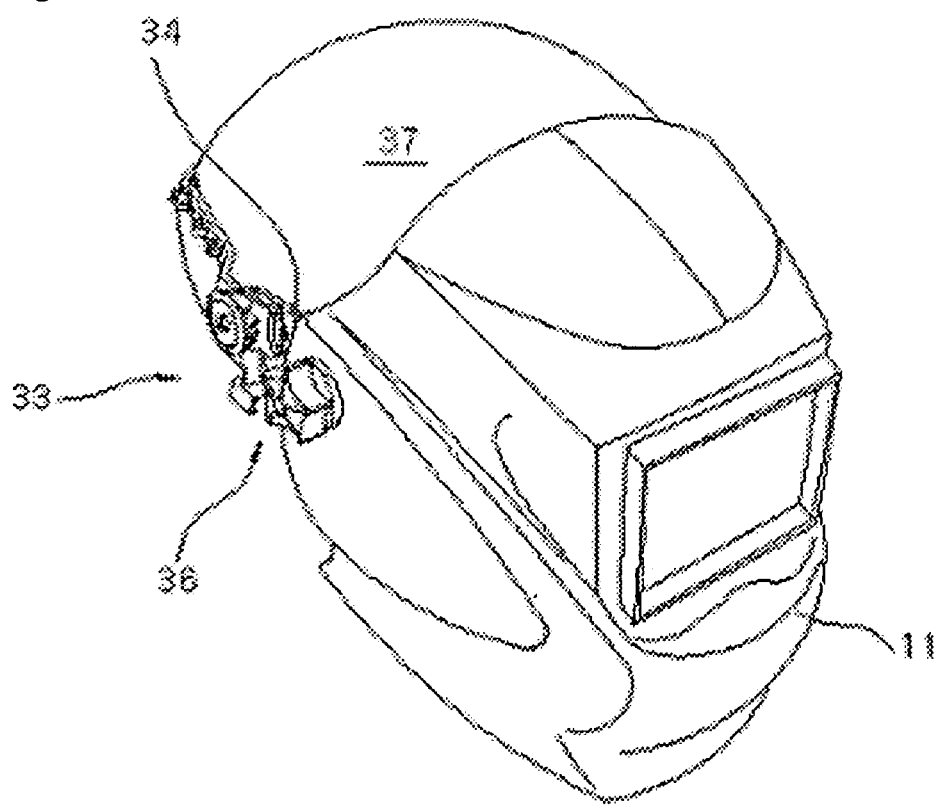
FIG. 4 is a perspective view illustrating a state in which a protective equipment is installed on the safety helmet using the multifunctional protection rack of the present invention.
Figure 5A:
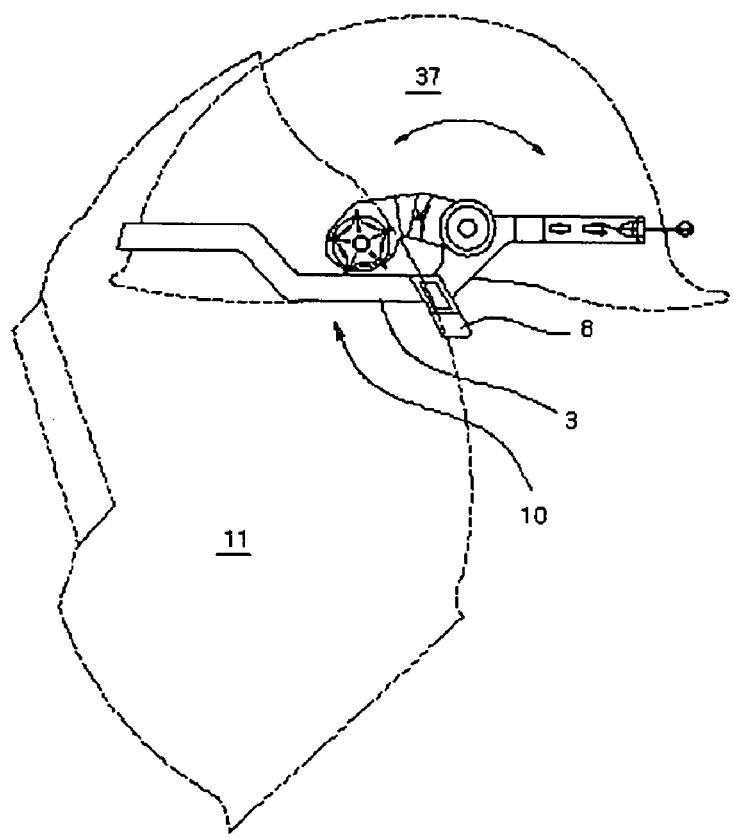
FIGS. 5A and 5B are schematic views respectively illustrating opening and closing operations of the welding mask.
Figure 5B:
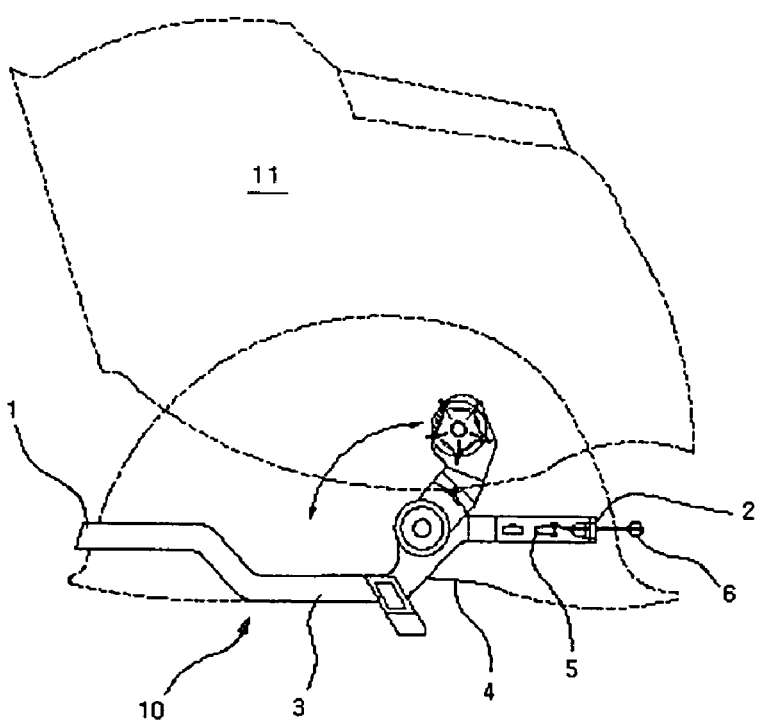
Figure 6:
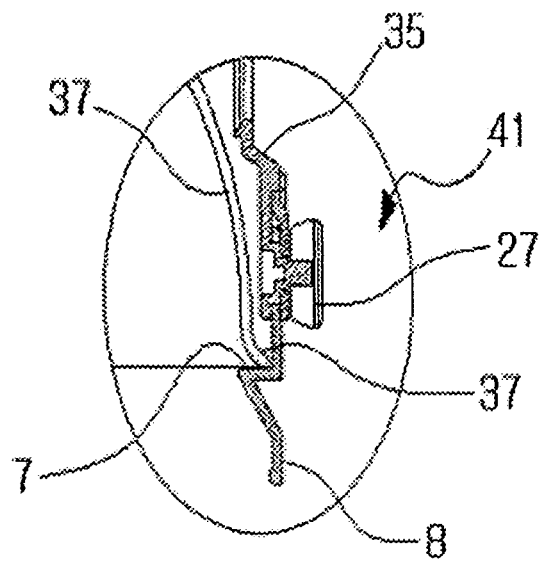
FIG. 6 is a sectional view illustrating a state in which a frame of the multifunctional protection rack of the present invention is connected to the safety helmet.
Figure 7:
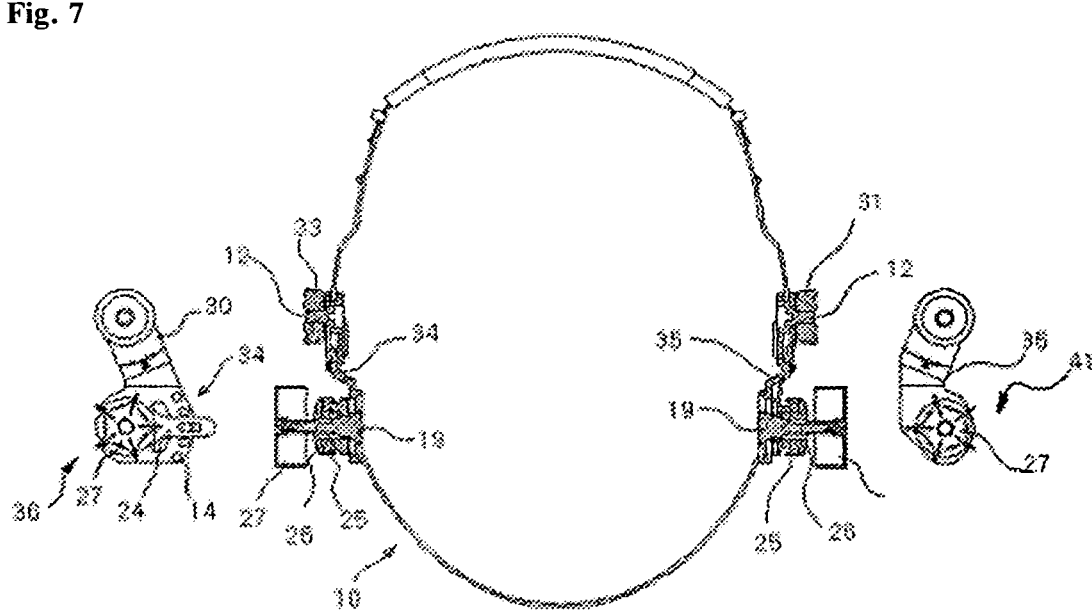
FIG. 7 is a sectional view of the multifunctional protection rack of the present invention.
Figure 8:
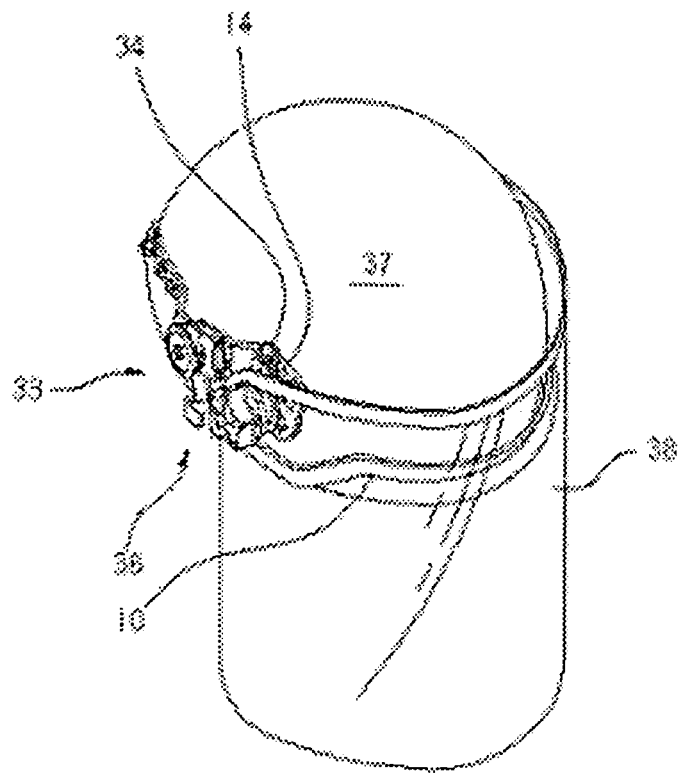
FIG. 8 is a perspective view illustrating a state in which another protective equipment (shield) is installed on a safety helmet using a multifunctional protection rack in accordance with another embodiment of the present invention.
Figure 9:
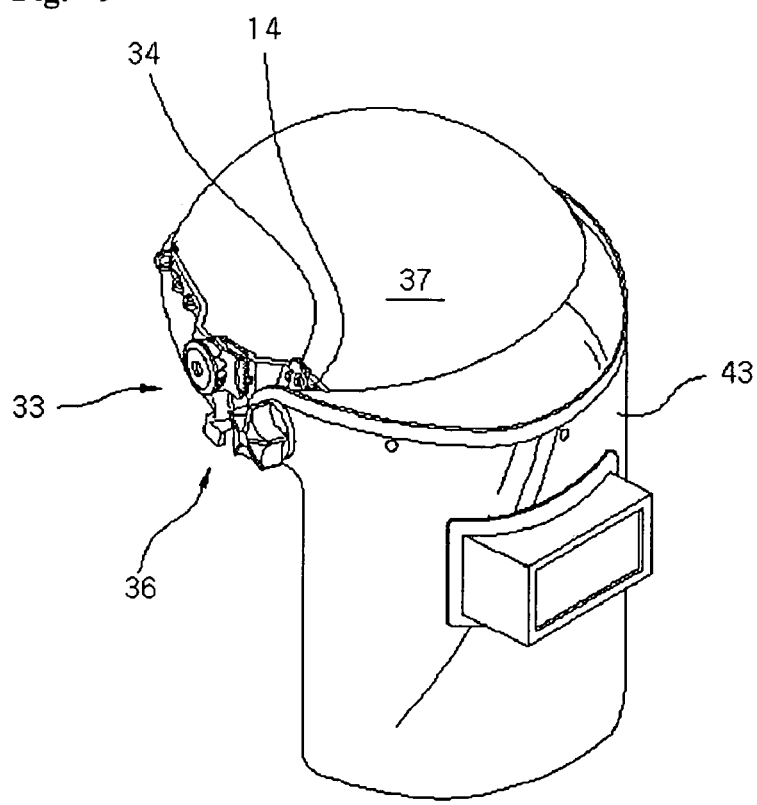
FIG. 9 is a perspective view illustrating a state in which yet another protective equipment (welding shield) is installed on a safety helmet using a multifunctional protection rack in accordance with yet another embodiment of the present invention.

FIG. 1 is a perspective view of a multifunctional protection rack for a safety helmet of the present invention. FIG. 2 is an exploded perspective view illustrating connection between a welding mask and the multifunctional protection rack in accordance with a preferred embodiment of the present invention. FIG. 3 is a perspective view of the multifunctional protection rack, which is installed on a safety helmet. FIG. 4 is a perspective view illustrating a state in which a protective equipment is installed on the safety helmet using the multifunctional protection rack. FIGS. 5A and 5B are schematic views respectively illustrating opening and closing operations of the welding mask. FIG. 6 is a sectional view illustrating a state in which a frame of the multifunctional protection rack is connected to the safety helmet. FIG. 7 is a sectional view of the multifunctional protection rack of the present invention. FIGS. 8 and 9 are perspective views, each of which illustrates a state in which another protective equipment is installed on a safety helmet using a multifunctional protection rack in accordance with another embodiment of the present invention.

As shown in FIGS. 1 to 9, the multifunctional protection rack of the present invention serves to obtain interchangeability of protective equipments (a protective goggle, a welding mask, a protective shield, a goggle, and a welding shield) installed on the safety helmet and to adjust a rotational radius of the installed protective equipment and an interval between the installed protective equipment and a worker's face for obtaining the worker's visual field. The multifunctional protection rack comprises a support frame 10 made of an elastic member formed along the outer surface of a visor of the safety helmet, which is bent into front and rear frames 1 and 2 and side support frames 3 so that the width of the support frame 10 can be adjusted, one connecting support member 34, one end of which is connected to the outer surface of the support frame 10 by a rotational angle adjusting portion 33 for adjusting a rotational angle, and the other end of which is connected to the outer surface of the support frame 10 by an interval adjusting portion 36 for adjusting an interval between a protective equipment and the worker's face, and another connecting support member 35 between the support frame 10 and the protective equipment, thereby being installed on a safety helmet 37 so that the protection rack can be opened and closed.

As shown in FIGS. 1, 5A, 5B, and 6, the support frame 10 installed on the safety helmet 37 is configured such that an elastic member, such as a coiled spring 6 or a rubber band, is connected between both ends of the rear frame 2 such that the elastic member is located at the same level as that of the front frame 1 bent along the front portion of the outer surface of the safety helmet 37, and a plurality of tension-adjusting holders 5 for fastening the elastic member are arranged such that tension is adjusted according to the size of the safety helmet 37. The side support frames 3 are connected between the front and rear frames 1 and 2 of the support frame 10 such that the side support frames 3 are protruded at a level lower than that of both side surfaces of the visor of the helmet 37 to surround the side surfaces of the visor of the helmet 37, and detachable bars 8, each of which is provided with a locking protrusion 7, are respectively formed along inner side surfaces of the side support frames 3, thereby supplying the load of the protective equipment to the safety helmet 37.

Now, with reference to FIGS. 1, 2, and 6, the configurations of the connecting support member 35, the rotational angle adjusting portion 33, and the interval adjusting portion 41, which are connected to the support frame 10, will be described. The connecting support member 35 is connected to a left installation hole 28 formed through the support frame 10. A fixing bolt 12 and an arc-structured stop gear 13 are formed on and in one portion of the connecting support member 35 so that the fixing bolt 12 and the stop gear 13 are inserted into the installation hole 28 of the support frame 10, and an extension hole 15 provided with square-shaped teeth is formed through the other portion of the connecting support member 35, which is bent from the above portion of the connecting support member 35 provided with the fixing bolt 12 and the stop gear 13.

The rotational angle adjusting portion 33 includes an angle adjusting washer 30, which is provided with a stop gear 29 formed on a protruding surface and a terminal thereof so that non-skid protrusions 23 are inserted into the angle adjusting washer 30, and a fixing nut 31 installed on the outer surface of the installation hole 28, into which the fixing bolt 12 is inserted, thereby being engaged with the stop gear 13.

A lock bolt 19 for fixing the protective equipment to the extension hole 15 of the connecting support member 35 includes an uneven portion 16 formed in the inner surface of its head part, an insert protrusion 17 provided with a thread formed therein, and a non-separation prominence 18 formed at the end of the insert protrusion 17 so that the lock bolt 19 is inserted into a washer 20 and a fixing bushing 25. The interval adjusting portion 41 is connected to the outer surface of the lock bolt 19 by an insert washer 26 provided with an insert groove 9, which is engaged with the insert protrusion 17 of the lock bolt 19, and a protruding nut 27.

Now, with reference to FIGS. 1 and 6, the configurations of the connecting support member 34, the rotational angle adjusting portion 33, and the interval adjusting portion 36, which are connected to the support frame 10, will be described. The connecting support member 34 is connected to a right installation hole 28 formed through the support frame 10. The fixing bolt 12 and the arc-structured stop gear 13 are formed on and in one portion of the connecting support member 34, and the extension hole 15 provided with square-shaped teeth is formed through the other portion of the connecting support member 14. A plurality of stop protrusions 14 are formed on the upper edge of the other portion of the connecting support member 34 above the extension hole 15.

The lock bolt 19 is inserted into the extension hole 15 such that the lock bolt 19 can move within the extension hole 15, and thus adjusts an interval between a protective equipment installed on the lock bolt 19 and a worker's face, thereby allowing the uneven portion 16 of the lock bolt 19 to be engaged with the square-shaped teeth in the extension hole 15.

That is, the lock bolt 19 inserted into the extension hole 15, a lock washer 24 including a fixing lever 22, provided with a through hole 21, formed therethrough and a non-skid protrusion 23, and the bushing 25 inserted into the lock washer 24 and a bushing hole 40 of a protective equipment are connected, a plurality of protrusions are formed on a contact portion of the bushing 25 so that the bushing 25 does not skid, and the corresponding one of the stop protrusions 14 is inserted into the through hole 21 of the fixing lever 22 so that the lock washer 24 is fixed and not to rotated.

Further, the interval adjusting portion 36 is connected to the outer surface of the lock bolt 19 by the insert washer 26 provided with the insert groove 9, which is engaged with the insert protrusion 17 of the lock bolt 19, and the protruding nut 27.

As shown in FIG. 8, in accordance with another embodiment of the present invention, a protective shield 38 is installed on the multifunctional protection rack.

Further, as shown in FIG. 9, in accordance with yet another embodiment of the present invention, a welding shield 43 is installed on the multifunctional protection rack. Additionally, other protective equipments may be conveniently attached to or detached from the multifunctional protection rack of the present invention.

Hereinafter, the function of the above-described multifunctional protection rack of the present invention will be described in detail.

As shown in FIGS. 1 to 7, in case that a welding mask is attached to a safety helmet using the multifunctional protection rack of the present invention, the multifunctional protection rack can be adjusted according to different worker's conditions, such as environments, working methods, and worker's physical conditions.

Further, as shown in FIGS. 5A and 5B, the multifunctional protection rack comprises a device for voluntarily adjusting an interval between a protective equipment and a worker's face so as to obtain interchangeability between various protective equipments (a protective goggle, a welding mask, a protective shield, and a goggle), to adjust a rotational radius of the protective equipment, which is installed on the safety helmet, and to obtain a visual field of the worker. Accordingly, in order to adjust the angle of the welding mask when the position of the welding mask is set, the fixing nut 31 of the rotational angle adjusting portion 33 is loosened, the angle adjusting washer 30 is engaged with the stop gear 29 at a desired position, and then the fixing nut 31 is screwed again so that the rotational angle adjusting portion 33 is fixed. Here, the non-skid protrusions 23 are formed on the surface of the angle adjusting washer 30 and the outer edge of the installation hole 28, thereby preventing the rotational angle adjusting portion 33 from being slipped. The left and right rotational angle adjusting portions 32 and 33 may be set to the same position or different positions by selection of a worker.

Then, the welding mask requires a fine interval with a worker's face according to the visual field of the worker and the welding position. Accordingly, as shown in FIGS. 1 and 5A, in order to obtain the visual field of the worker and the circulation or air through the welding mask, the protruding nut 27 is loosened by rotating it in the counterclockwise direction, and the lock bolt 19 moves within the extension hole 15 of the connecting support member 34. Then, the fixing lever 22 of the lock wash 24 is rotated and fixed by inserting the stop protrusion 14 into the through hole 21, the insert protrusion 17 of the lock bolt 19 is inserted into the insert groove 9 of the insert washer 26, and the protruding nut 27 is rotated in the clockwise direction. Thereby, it is possible to adjust the interval between the welding mask and the worker's face. Further, since the lock washer 24 is installed on one portion of the left connecting support member 35, only the lock bolt 19 moves within the extension hole 15, and then the left connecting support member 35 is fixed using the protruding nut 27 through the above-described process.

By using the above method, it is possible to adjust the rotational angle of the protective equipment and the interval between the protective equipment and the worker's face.

As apparent from the above description, the present invention provides a multifunctional protection rack for a safety helmet, in which a protective equipment is installed on the safety helmet under the condition that a worker wears the safety helmet, so as to obtain interchangeability between various protective equipments and to be easily attached to and detached from the safety helmet.

Further, the multifunctional protection rack of the present invention adjusts an interval between the installed protective equipment and a worker's face and an angle of the installed protective equipment so as to satisfy working conditions of the worker wearing the safety helmet, and is detachably installed on all kinds of safety helmets.

Moreover, the multifunctional protection rack of the present invention, installed on the safety helmet, has an ergonomic structure such that the installed position of the welding mask is not changed, thereby being efficiently used in a protective equipment field.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A protective device holder for attachment to a safety helmet comprising:
    an elastic support frame formed into front, rear frames and side whereby the width of the support frame can be adjusted to conform to an outer surface of a safety helmet, said rear frame comprising a spring, and tension-adjusting holders for adjusting tension in said spring;
    first and second device connectors respectively attached to opposite sides of said support frame, said device connectors each including an angle adjusting portion for adjusting a rotational angle of a protective device to be attached to the holder and a distance adjusting portion for adjusting distance between the protective device and the face of a worker wearing the safety helmet, said distance adjusting portion extending forwardly from said angle adjusting portion.

2. The holder of claim 1, further comprising resilient helmet connectors each having a locking protrusion for inwardly extending under a side edge of a safety helmet to detachably secure said support frame to a safety helmet.

3. The holder of claim 1, wherein said angle adjusting portions each include a fixing bolt and a stop gear inserted into an installation hole formed through the support frame.

4. The holder of claim 2, wherein said angle adjusting portions each include a fixing bolt and a stop gear inserted into an installation hole formed through the support frame.

5. The holder of claim 1 wherein said distance adjusting portions each include an extension hole through said forwardly extending portion, said hole having inwardly extending teeth, and a lock bolt, for connecting a protective device to the device holder, said lock bolt having a head, a shank having an uneven portion inwardly of said head and a thread, a non-separation prominence formed at the end of the shank whereby said lock bolt may be inserted into a washer and fixing bushing of the protective device, an insert washer having with an insert groove engaged with the shank of the lock bolt, and a nut for fastening the lock bolt into said insert washer.

6. The holder of claim 2 wherein said distance adjusting portions each include an extension hole through said forwardly extending portion, said hole having inwardly extending teeth, and a lock bolt, for connecting a protective device to the device holder, said lock bolt having a head, a shank having an uneven portion inwardly of said head and a thread, a non-separation prominence formed at the end of the shank whereby said lock bolt may be inserted into a washer and fixing bushing of the protective device, an insert washer having with an insert groove engaged with the shank of the lock bolt, and a nut for fastening the lock bolt into said insert washer.

7. The holder of claim 3 wherein said distance adjusting portions each include an extension hole through said forwardly extending portion, said hole having inwardly extending teeth, and a lock bolt, for connecting a protective device to the device holder, said lock bolt having a head, a shank having an uneven portion inwardly of said head and a thread, a non-separation prominence formed at the end of the shank whereby said lock bolt may be inserted into a washer and fixing bushing of the protective device, an insert washer having with an insert groove engaged with the shank of the lock bolt, and a nut for fastening the lock bolt into said insert washer.

8. The holder of claim 4 wherein said distance adjusting portions each include an extension hole through said forwardly extending portion; said hole having inwardly extending teeth, and a lock bolt, for connecting a protective device to the device holder, said lock bolt having a head, a shank having an uneven portion inwardly of said head and a thread, a non-separation prominence formed at the end of the shank whereby said lock bolt may be inserted into a washer and fixing bushing of the protective device, an insert washer having with an insert groove engaged with the shank of the lock bolt, and a nut for fastening the luck bolt into said insert washer.

9. The protective device holder of claim 1 in combination with a protective device comprising one of a welding mask, a light shield and a welding shield.

* * * * *